(12) United States Patent
Maehara et al.

(10) Patent No.: US 10,117,788 B2
(45) Date of Patent: Nov. 6, 2018

(54) TRANSPORT METHOD, MANUFACTURING METHOD FOR DISPOSABLE WEARABLE ARTICLE, AS WELL AS WEARABLE ARTICLE, AND TRANSPORT DEVICE

(71) Applicant: ZUIKO CORPORATION, Settsu-shi, Osaka (JP)

(72) Inventors: Toshiyuki Maehara, Osaka (JP); Kazutoshi Makimura, Osaka (JP); Toyoshi Umebayashi, Osaka (JP)

(73) Assignee: ZUIKO CORPORATION, Settsu-Shi, Osaka (JP)

( * ) Notice: Subject to any disclaimer, the term of this patent is extended or adjusted under 35 U.S.C. 154(b) by 414 days.

(21) Appl. No.: 14/408,828

(22) PCT Filed: Jun. 19, 2013

(86) PCT No.: PCT/JP2013/003828
§ 371 (c)(1),
(2) Date: Dec. 17, 2014

(87) PCT Pub. No.: WO2014/006834
PCT Pub. Date: Jan. 9, 2014

(65) Prior Publication Data
US 2015/0223992 A1     Aug. 13, 2015

(30) Foreign Application Priority Data

Jul. 6, 2012   (JP) .................. 2012-152655

(51) Int. Cl.
*A61F 13/15*     (2006.01)
*B32B 38/00*    (2006.01)
(Continued)

(52) U.S. Cl.
CPC ........ *A61F 13/15764* (2013.01); *A61F 13/15* (2013.01); *A61F 13/49* (2013.01);
(Continued)

(58) Field of Classification Search
CPC .............. A61F 13/15764; B32B 37/18; B32B 38/0004; B32B 38/18; Y10T 156/1052; Y10T 156/1062
See application file for complete search history.

(56) References Cited

U.S. PATENT DOCUMENTS 4,726,876 A * 2/1988 Tomsovic, Jr. ... A61F 13/15601
156/552
4,824,498 A * 4/1989 Goodwin ........... A47G 27/0468
156/71

(Continued)

FOREIGN PATENT DOCUMENTS

EP     0439897 A1    8/1991
EP     1162162 A1   12/2001
(Continued)

OTHER PUBLICATIONS

International Search Report dated Sep. 6, 2013.

*Primary Examiner* — Mark A Osele
*Assistant Examiner* — Christopher C Caillouet
(74) *Attorney, Agent, or Firm* — Gerald E. Hespos; Michael J. Porco; Matthew T. Hespos

(57) ABSTRACT

The transport method includes a speed varying step of varying speed of a first holding portion between a receiving position and a predetermined relay position by means of a speed change mechanism; a control step of controlling speed of a servo motor for driving rotation of second holding portions, such that speed of the second holding portions becomes a receiving speed at which the second holding portions is able to receive the absorbent body from the first holding portion at the relay position and becomes a predetermined transfer speed at a transfer position, and such that the second holding portions arrive at the relay position and (Continued)

at the transfer position at a predetermined cycle; and a speed changing step of changing the transfer speed while the cycle is maintained.

6 Claims, 12 Drawing Sheets

(51) Int. Cl.
    *B32B 38/18*     (2006.01)
    *B65H 39/14*     (2006.01)
    *A61F 13/49*     (2006.01)
    *B32B 37/00*     (2006.01)
    *B32B 37/12*     (2006.01)
    *B32B 37/18*     (2006.01)

(52) U.S. Cl.
    CPC ...... *B32B 37/0076* (2013.01); *B32B 37/1292* (2013.01); *B32B 37/18* (2013.01); *B32B 38/0004* (2013.01); *B32B 38/18* (2013.01); *B65H 39/14* (2013.01); *A61F 2013/1591* (2013.01); *B32B 2555/02* (2013.01); *B65H 2301/33216* (2013.01); *B65H 2301/33222* (2013.01); *B65H 2406/3454* (2013.01); *B65H 2801/57* (2013.01); *Y10T 156/1052* (2015.01)

(56) References Cited

U.S. PATENT DOCUMENTS

| | | |
|---|---|---|
| 5,025,910 A | 6/1991 | Lasure |
| 5,643,396 A | 7/1997 | Rajala |
| 5,660,657 A | 8/1997 | Rajala |
| 6,450,321 B1 | 9/2002 | Blumenthal et al. |
| 6,482,278 B1 * | 11/2002 | McCabe ........... A61F 13/15609 156/200 |
| 2002/0023723 A1 | 2/2002 | Blumenthal et al. |
| 2002/0125105 A1 | 9/2002 | Nakakado |
| 2002/0175047 A1 | 11/2002 | Blumenthal et al. |
| 2003/0010423 A1 | 1/2003 | Nakakado |
| 2003/0066609 A1 * | 4/2003 | Calvert ............. A61F 13/15772 156/362 |
| 2004/0089516 A1 * | 5/2004 | Christian ........... A61F 13/15723 198/459.8 |
| 2007/0074953 A1 | 4/2007 | McCabe |
| 2008/0196564 A1 * | 8/2008 | McCabe ........... A61F 13/15723 83/23 |

FOREIGN PATENT DOCUMENTS

| | | |
|---|---|---|
| EP | 1260203 A2 | 11/2002 |
| EP | 1325725 A2 | 7/2003 |
| JP | 2006-212307 | 8/2006 |
| JP | 4054191 | 12/2007 |
| JP | 2008-246138 | 10/2008 |
| JP | 2012-125587 | 7/2012 |

* cited by examiner

TRANSPORT METHOD, MANUFACTURING METHOD FOR DISPOSABLE WEARABLE ARTICLE, AS WELL AS WEARABLE ARTICLE, AND TRANSPORT DEVICE

TECHNICAL FIELD

The present invention relates to a technology for transporting processing parts received at a predetermined receiving position to a predetermined transfer position, with the speed of the processing parts varying between the receiving position and the transfer position.

BACKGROUND ART

Transport devices are hitherto known as described, for example, in Japanese Patent No. 4054191.

The transport device described in Japanese Patent No. 4054191 includes a drive wheel driven by a motor to rotate at constant speed, a plurality of suction members each attached to the drive wheel via a crank arm and configured to hold processed articles, and a base part that rotatably supports the drive wheel.

Each of the crank arms is attached to the drive wheel such as to be rotatable around a rotation center axis that is parallel to that of the drive wheel. A cam roller is provided for changing speeds, at a position away from the rotation center of each crank arm, to be movable along a speed-changing cam groove formed in the base part. The speed-changing cam groove is formed eccentrically to the center of the drive wheel.

Thus, the distance from the center of the drive wheel to each speed-changing cam roller changes periodically in accordance with the positional relationship between the speed-changing cam roller and the speed-changing cam groove. Namely, the crank arm moves forward or backward in the rotating direction of the drive wheel as the drive wheel rotates. Angular velocity of each of suction member changes due to this movement (swing) as the drive wheel rotates.

This way, with the transport device described in Japanese Patent No. 4054191, processed articles received at a receiving position are transported to a transfer position, with the speed of the processed articles being varied between the receiving position and the transfer position.

However, in this transport device described in Japanese Patent No. 4054191, the speed change of each suction member is achieved by a mechanical configuration (speed-changing cam roller and cam groove). Therefore, it is difficult to set a plurality of speeds of the processed articles at the transfer position.

More specifically, It is conceived that the processed articles could be transported at a plurality of speeds by varying the angular velocity of the motor that rotates the drive wheel described in Japanese Patent No. 4054191. However, changing the angular velocity of the drive wheel that carries a plurality of suction members requires a large torque, and a motor that can be accelerated and decelerated in a short time would be needed. Motors that can satisfy these conditions are hard to be secured.

It would be possible to set a plurality of speeds of the processed articles at the transfer position by driving the motor at a constant speed higher, or lower, than usual in the transport device described in Japanese Patent No. 4054191. This, however, would lead to a variation in the quantity of transported articles per unit time, because changing the motor speed would vary the cycle of each suction member (processed article) arriving at the transfer position.

Therefore, in order to change speed of each suction member while maintaining the transport quantity per unit time in the transport device of Japanese Patent No. 4054191, it would be necessary to prepare many kinds of the mechanical configurations described above for each of several target speeds. This would increase the facility cost, and also the operation time, since it is necessary to change the mechanical configurations every time the speed is changed.

SUMMARY OF INVENTION

An object of the present invention is to provide a transport method whereby processing parts can be transported to a transfer position at various different speeds while the quantity of the processing parts to be transported per unit time is maintained, a method of manufacturing disposable wearable articles, a wearable article, and a transport device.

The present invention provides a transport method of transporting a processing part from a predetermined receiving position to a predetermined transfer position, the transport method including: a speed varying step of varying speed of a first holding portion between the receiving position and a predetermined relay position by means of a speed change mechanism, by rotating, at constant speed, a drive wheel on which the first holding portion that is configured to receive the processing part at the receiving position is supported via the speed change mechanism; a control step of controlling speed of a holding portion drive source for driving rotation of a second holding portion configured to hold the processing part, such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle; and a speed changing step of changing the transfer speed while the cycle is maintained.

The present invention also provides a transport device for transporting a processing part from a predetermined receiving position to a predetermined transfer position, the transport device including: a speed change device including a first holding portion configured to receive a processing part at the receiving position, a drive wheel supporting the first holding portion, a drive source for the drive wheel for rotating the drive wheel at constant speed, and a speed change mechanism interposed between the first holding portion and the drive wheel to vary speed of the first holding portion between the receiving position and a predetermined relay position as the drive wheel rotates at constant speed; and a rotation control device including a second holding portion configured to hold the processing part, a holding portion drive source for driving rotation of the second holding portion, and a control unit that controls speed of the holding portion drive source such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle, wherein the control unit of the rotation control device is configured to change the transfer speed while maintaining the cycle.

Furthermore, the present invention provides a method of manufacturing a disposable wearable article having a basic part and a processing part joined on the basic part, the method including: a web transport step of transporting a basic part web for forming the basic part; a processing part transport step of transporting the processing part from a predetermined receiving position to a predetermined transfer position, such that the processing part is received at the receiving position and transferred, at the transfer portion, onto the basic part web that is being transported in the web transport step; a joining step of joining the processing part to the basic part web; and a cutting step of cutting the basic part web to the basic part, wherein the processing part transport step includes: a speed varying step of varying speed of a first holding portion between the receiving position and a predetermined relay position by means of a speed change mechanism, by rotating, at constant speed, a drive wheel on which the first holding portion that is configured to receive the processing part at the receiving position is supported via the speed change mechanism; a control step of controlling speed of a holding portion drive source for driving rotation of a second holding portion configured to hold the processing part, such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle; and a speed changing step of changing the transfer speed while the cycle is maintained, and wherein, in the web transport step, the basic part web is transported at a speed that allows the processing part to be received at the transfer position.

The present invention also provides a wearable article manufactured by the manufacturing method described above.

According to the present invention, processing parts can be transported to a transfer position at various different speeds while the quantity of the processing parts to be transported per unit time is maintained.

DESCRIPTION OF EMBODIMENTS

Embodiments of the present invention will be hereinafter described with reference to the accompanying drawings. The following embodiments are only examples of embodiment of the present invention and not of the nature that limits the technical scope of the present invention.

Figure 1:
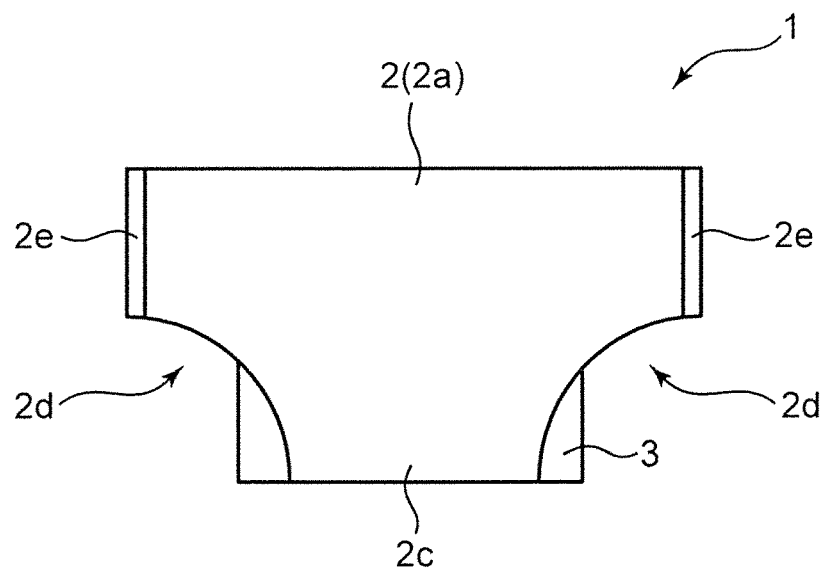
FIG. 1 is a schematic front view of a disposable diaper according to an embodiment of the present invention.
Figure 2:
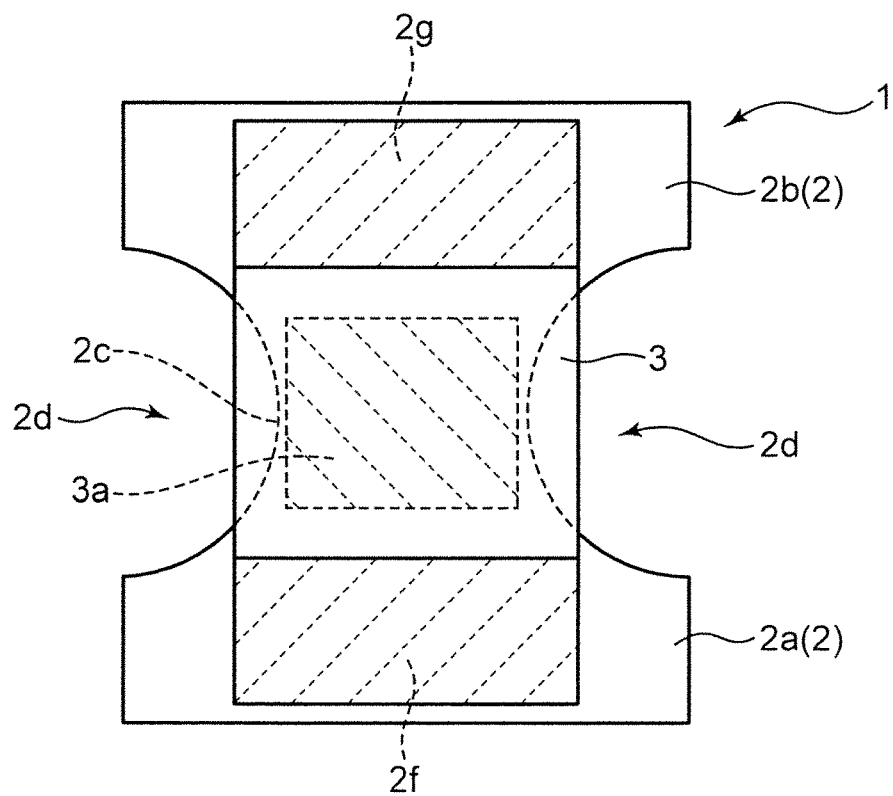
FIG. 2 is a developed view of the disposable diaper shown in FIG. 1.

FIG. 1 and FIG. 2 illustrate a disposable diaper 1, which is one example of a wearable article according to the present invention.

Referring to both drawings, the disposable diaper 1 is a type known as a pants diaper. More specifically, the disposable diaper 1 includes a diaper body (basic part) 2 and an absorbent body (processing part) 3 joined on the diaper body 2.

The diaper body 2 includes a front abdominal portion 2a that is placed on the abdominal of a wearer, a back portion 2b that is placed on the hip of the wearer, and a crotch portion 2c that is placed on the crotch of the wearer. Both end potions of the front abdominal portion 2a in a front-and-back direction are joined to both end portions of the back portion 2b in the front-and-back direction, respectively, via side seals 2e. On the left and right sides of the crotch portion 2c of the diaper body 2 are formed leg holes (through holes) 2d. The front abdominal portion 2a and the back portion 2b are stretchable in a left-right direction. More specifically, the front abdominal portion 2a and the back portion 2b may be formed of a material that is elastic itself (elastic non-woven cloth), or formed by attaching an elastic member between a pair of non-woven cloth sheets in a state where the elastic member is stretched. The elastic member may be made of polyurethane, natural rubber, thermoplastic resin, and the like. The elastic member may be in the form of a string, or a ribbon.

The absorbent body 3 is joined on the diaper body 2 between both leg holes 2d, in a developed state shown in FIG. 2, such as to cover inner side portions of the leg holes 2d (parts of leg holes 2d closer to each other). More specifically, the absorbent body 3 is bonded to the diaper body 2 in a front bonding portion 2f, a rear bonding portion 2g, and a center bonding portion 3a. Both end portions in the front-and-back direction of the absorbent body 3 are bonded to the diaper body 2 in the front and rear bonding portions 2f and 2g. A central portion in the front-and-back direction of the absorbent body 3 is bonded to the diaper body 2 in the center bonding portion 3a between the front and rear bonding portions 2f and 2g. The center bonding portion 3a is positioned between both leg holes 2d.

The absorbent body 3 is configured to absorb urine or the like of the wearer. More specifically, the absorbent body 3 includes, although not shown, a liquid permeable top sheet provided on an inner side, a liquid impermeable cover sheet provided on an outer side, and an absorbent core provided between these sheets. Thus urine or the like that has penetrated through the top sheet is absorbed by the absorbent core. The top sheet may be made of liquid permeable non-woven cloth or a mesh sheet. The cover sheet may be made of air permeable polyethylene film, or water repellent and air permeable non-woven cloth, or a laminated sheet of these. The absorbent core may be made by laminating fluff pulp produced through crushing and defibration of roll pulp. Super absorbent polymer may be mixed to the fluff pulp.

While a pants-type disposable diaper 1 is shown as one example in this embodiment which has a front abdominal portion 2a and a back portion 2b joined via side seals 2e, the invention is not limited to this. The disposable diaper may be a tape-type, which has fastening tapes instead of side seals 2e so that the front abdominal portion 2a and the back portion 2b are removably joined together by the fastening tapes. While the disposable diaper 1 illustrated here as one example has a diaper body 2 with a front abdominal portion 2a, a back portion 2b, and a crotch portion 2c, the invention is not limited to this. The disposable diaper 1 may have a diaper body 2 with a front abdominal portion 2a and a back portion 2b that are separate from each other, and an absorbent body 3 that connects the front abdominal portion 2a and the back portion 2b.

A method of manufacturing the disposable diaper 1 will now be described below with reference to FIG. 3 and FIG. 4.

The method of manufacturing disposable diapers 1 includes a web transport step (1) of transporting a body web (basic part web) 2A for forming diaper bodies 2, a first application step (2) of applying adhesive on the body web 2A, a leg hole forming step (through hole forming step) (3) of forming leg holes 2d in the body web 2A, a continuous body transport step (4) of transporting a continuous body 3A formed by the absorbent bodies 3 that are continuous in a lengthwise direction, a second application step (5) of applying adhesive on the continuous body 3A, a continuous body cutting step (6) of cutting the continuous body 3A, an absorbent body transport step (7) of transporting the absorbent bodies 3 to the body web 2A, a joining step (8) of joining the absorbent bodies 3 to the body web 2A, a folding step (9) of folding the body web 2A in two, a side seal step (10) of forming the side seals 2e, and a body cutting step (11) of cutting the body web 2A.

In the web transport step (1), until the body cutting step (11) is performed, the body web 2A is transported in its longitudinal direction, with a predetermined tension being applied to the body web 2A. In the following description, a direction orthogonal to the transport direction of the body web 2A may be referred to as a web width direction.

In the first application step (2), the adhesive is applied to an area of the body web 2A other than a region where a leg hole 2d is to be formed. More specifically, in the first application step (2), the adhesive is applied to two web-side bonding positions (corresponding to the front bonding portion 2f and rear bonding portion 2g), which correspond to positions of both end portions of the absorbent body 3 to be placed on the body web 2A in the joining step (8) that is described later. In this embodiment, the first application step is performed with the use of a first applicator 16 shown in FIG. 4.

In the leg hole forming step (3), a series of leg holes 2d are formed successively in the body web 2A at a distance in the transport direction of the body web 2A. More specifically, in this embodiment, leg holes 2d are formed in the body web 2A with the use of a leg hole forming member 17 shown in FIG. 4. The leg hole forming member 17 includes a rotary cutter 17a having cutter blades along the outer periphery, and an anvil 17b for pressing the body web 2A between itself and the rotary cutter 17a.

In the continuous body transport step (4), until the continuous body cutting step (6) is performed, the continuous body 3A is transported in its longitudinal direction, with a predetermined tension being applied to the continuous body 3A.

In the second application step (5), the adhesive is applied to an area of the continuous body 3A (absorbent body 3) other than an area that is to cover the leg holes 2d, which is a position between portions corresponding to the front bonding portion 2f and rear bonding portion 2g (corresponding to the center bonding portion 3a). More specifically, in this embodiment, the second application step (5) is performed with the use of a second applicator 14 shown in FIG. 4 during the continuous body transport step (4).

In the continuous body cutting step (6), the continuous body 3A is cut into absorbent bodies 3. More specifically, in this embodiment, the continuous body 3A is cut by pressing the continuous body 3A between a cutting roller 15 having cutter blades along the outer periphery and a speed change device 11 to be described later, as shown in FIG. 4. In other words, in this embodiment, an absorbent body 3 is transferred to the speed change device 11 while the absorbent body 3 is cut from the continuous body 3A.

Figure 3:
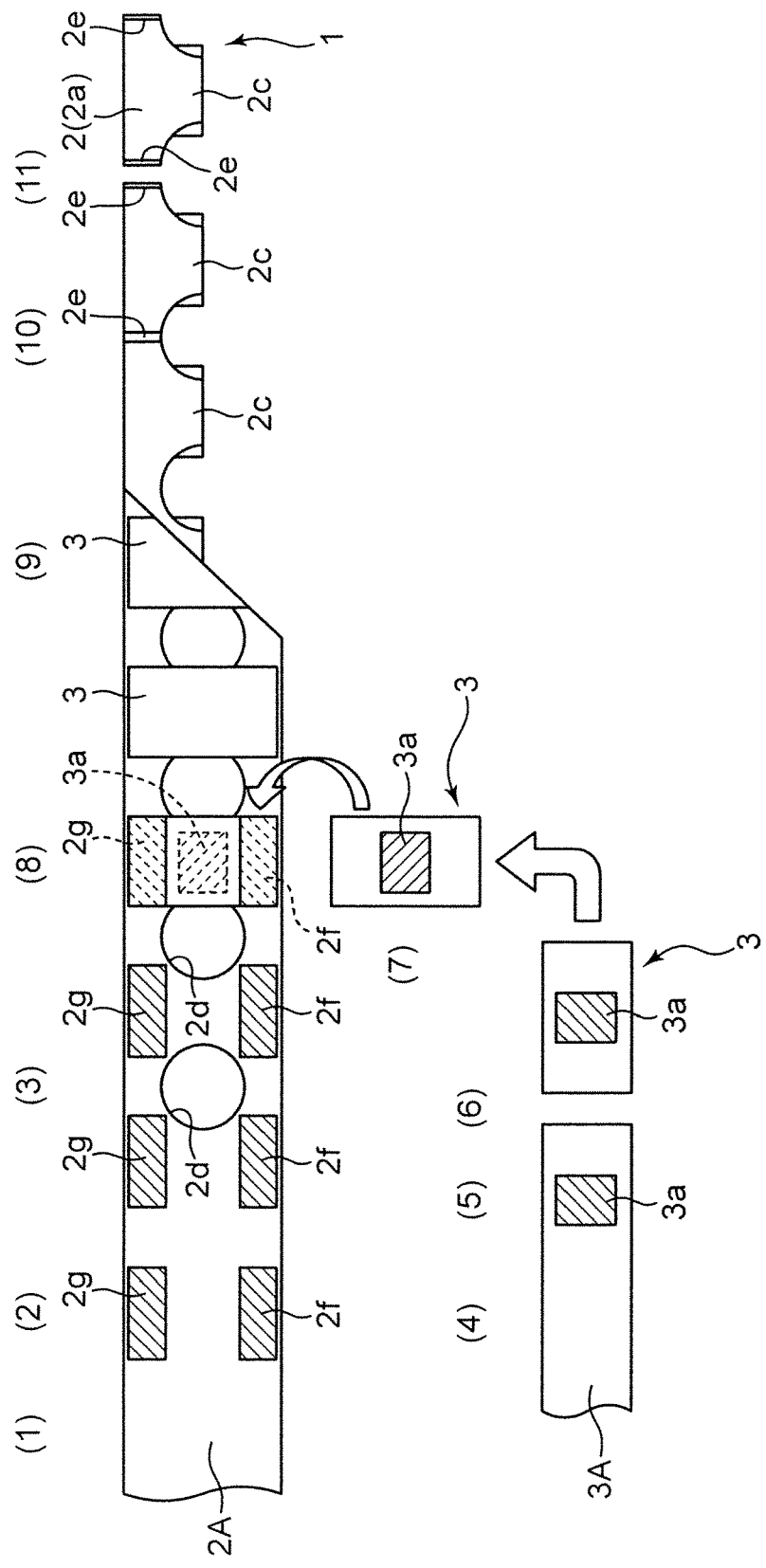
FIG. 3 is a process diagram illustrating a method of manufacturing the disposable diaper shown in FIG. 1.

In the absorbent body transport step (7), the longitudinal direction of the absorbent body 3 is rotated 90° as shown in FIG. 3, and the absorbent body 3 is transported onto the body web 2A. More specifically, in the absorbent body transport step (7), as shown in FIG. 4, the absorbent body 3 is transported from a predetermined receiving position E1 to a predetermined transfer position E3 such that the absorbent body 3 is received at the receiving position E1, and transferred onto the body web 2A at the transfer position E3. In this embodiment, the absorbent body transport step (7) is performed with the use of a transport device 10.

The transport device 10 includes a speed change device 11 that transports the absorbent bodies 3 from the receiving position E1 to a predetermined relay position E2, and a rotation control device 12 that transports the absorbent bodies 3 from the relay position E2 to the transfer position E3. The speed change device 11 will be described below with reference to FIG. 4 to FIG. 6.

The speed change device 11 includes eight first holding portions 20 each configured to receive an absorbent body 3 at the receiving position E1, a drive wheel 19 supporting the respective first holding portions 20, a drive wheel motor (drive source for the drive wheel) 18 for rotating the drive wheel 19 at constant speed, and a speed change mechanism (no reference numeral provided) interposed between the first holding portions 20 and the drive wheel 19 to vary the speed of the first holding portions 20 between the receiving position E1 and the relay position E2 by rotating the drive wheel 19 at constant speed.

Figure 6:
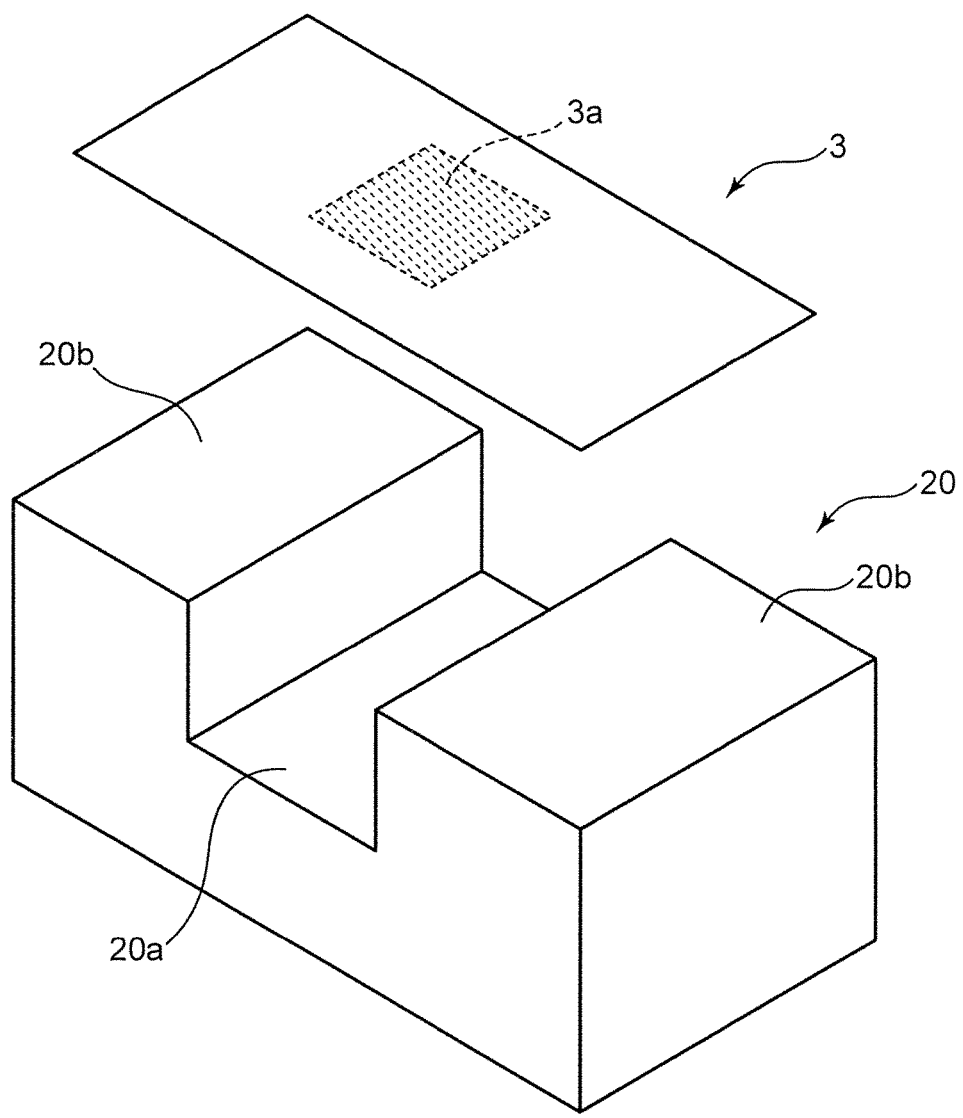
FIG. 6 is a perspective view illustrating a holding pad shown in FIG. 5 to a larger scale.

The first holding portions 20 are arranged on a radially outer side of the drive wheel 19 around the rotation center axis of the drive wheel 19. A negative pressure is supplied from a suction source outside of the drawing so that the first holding portions 20 can hold the absorbent bodies 3 by suction on outer circumferential surfaces of the first holding portions 20. More specifically, the first holding portion 20 includes a pair of suction surfaces 20b for holding both end portions of the absorbent body 3 in a longitudinal direction (web width direction) by suction, as shown in FIG. 6. On a portion of outer surface of the first holding portion 20 between the suction surfaces 20b is formed an escape groove 20a to avoid contact with adhesive applied to an area corresponding to the center bonding portion 3a of the absorbent body 3.

The speed change mechanism includes eight crank arms 21 rotatably attached to the drive wheel 19, eight links 22 each rotatably attached to each of the crank arms 21, and a fixed member (no reference numeral provided) formed with a speed-changing cam groove 23 for swinging the crank arms 21. Each crank arm 21 includes an arm body 21a, and a cam roller 21b provided on the arm body 21 to allow the cam roller 21b to move along the speed-changing cam groove 23. The arm body 21a has a base end portion attached to the drive wheel 19 such as to be rotatable around a rotation axis 21c parallel to the rotation center axis of the drive wheel 19. The cam roller 21b is provided on the arm body 21a away from the rotation axis 21c. The speed-changing cam groove 23 is formed in the fixed member that rotatably supports the drive wheel 19 eccentrically to the center of the drive wheel 19. Thus, the distance from the rotation center axis of the drive wheel 19 to each cam roller 21b changes periodically in accordance with the positional relationship between the cam roller 21b and the speed-changing cam groove 23. More specifically, the distal end portion of each arm body 21a moves forward or backward in the rotating direction of the drive wheel 19 as the drive wheel 19 rotates at constant speed. By this reciprocal movement (swing), the angular velocity of the first holding portions 20 that are connected to the arm bodies 21a via links 22 is changed between the receiving position E1 and the relay position E2 (speed varying step).

The link 22 has a base end portion attached to the distal end portion of the crank arm 21 such as to be rotatable around an axis parallel to the rotation center axis of the drive wheel 19. The distal end portion of each link 22 is attached to each of the first holding portions 20 such as to be rotatable around an axis parallel to the rotation center axis of the drive wheel 19.

The speed change device 11 according to this embodiment includes a turning mechanism outside of the drawing that rotates the first holding portions 20 90° around a normal line of the suction surfaces 20b of the first holding portions 20. Thus the speed change device 11 can transfer the absorbent body 3 to the rotation control device 12 at the relay position E2 after changing the orientation of the absorbent body 3 received at the receiving position E1 such that the longitudinal direction of the absorbent body 3 is turned 90°.

Figure 7:
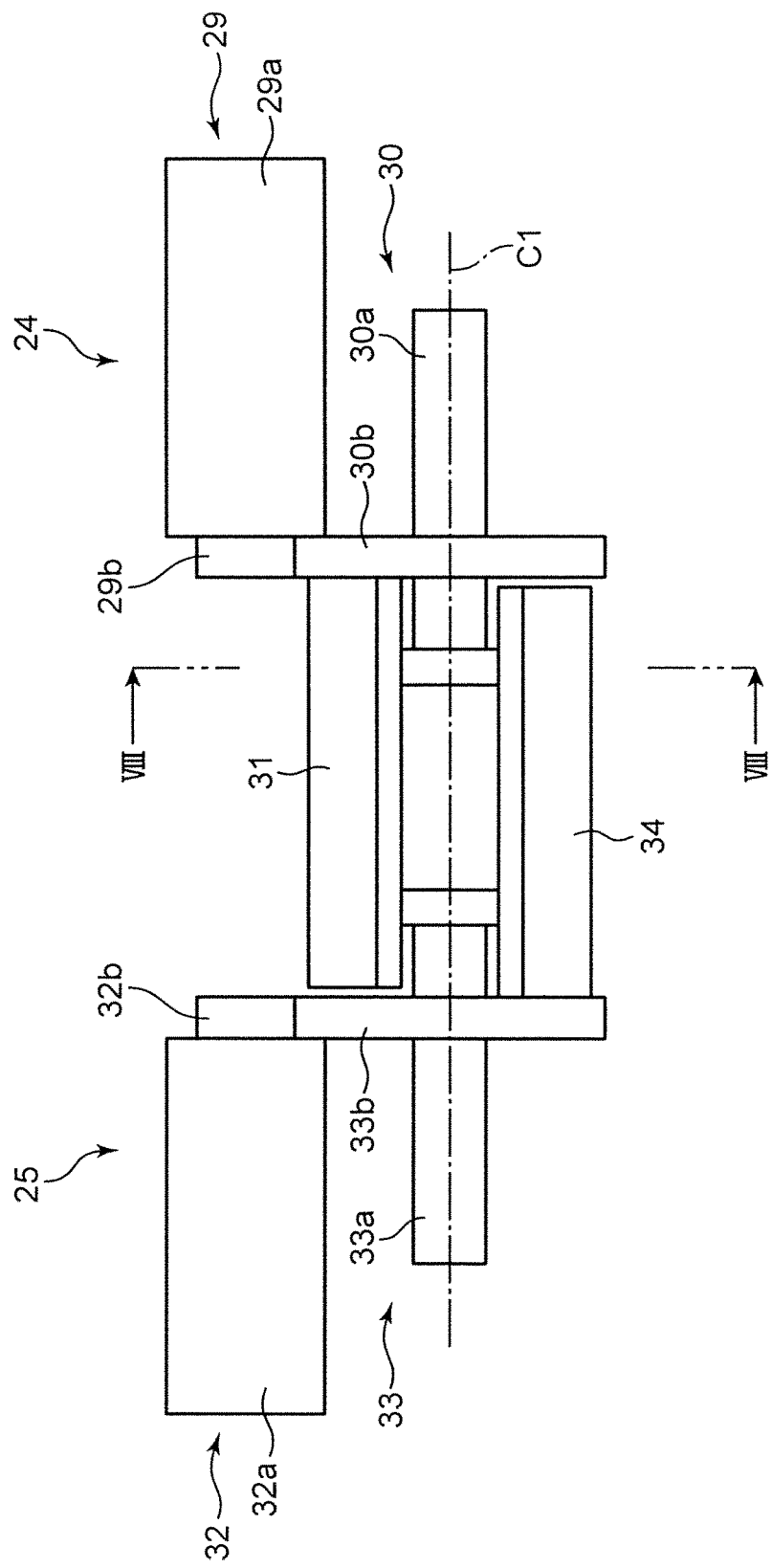
FIG. 7 is a front view illustrating a schematic configuration of a rotation control device shown in FIG. 4.
Figure 8:
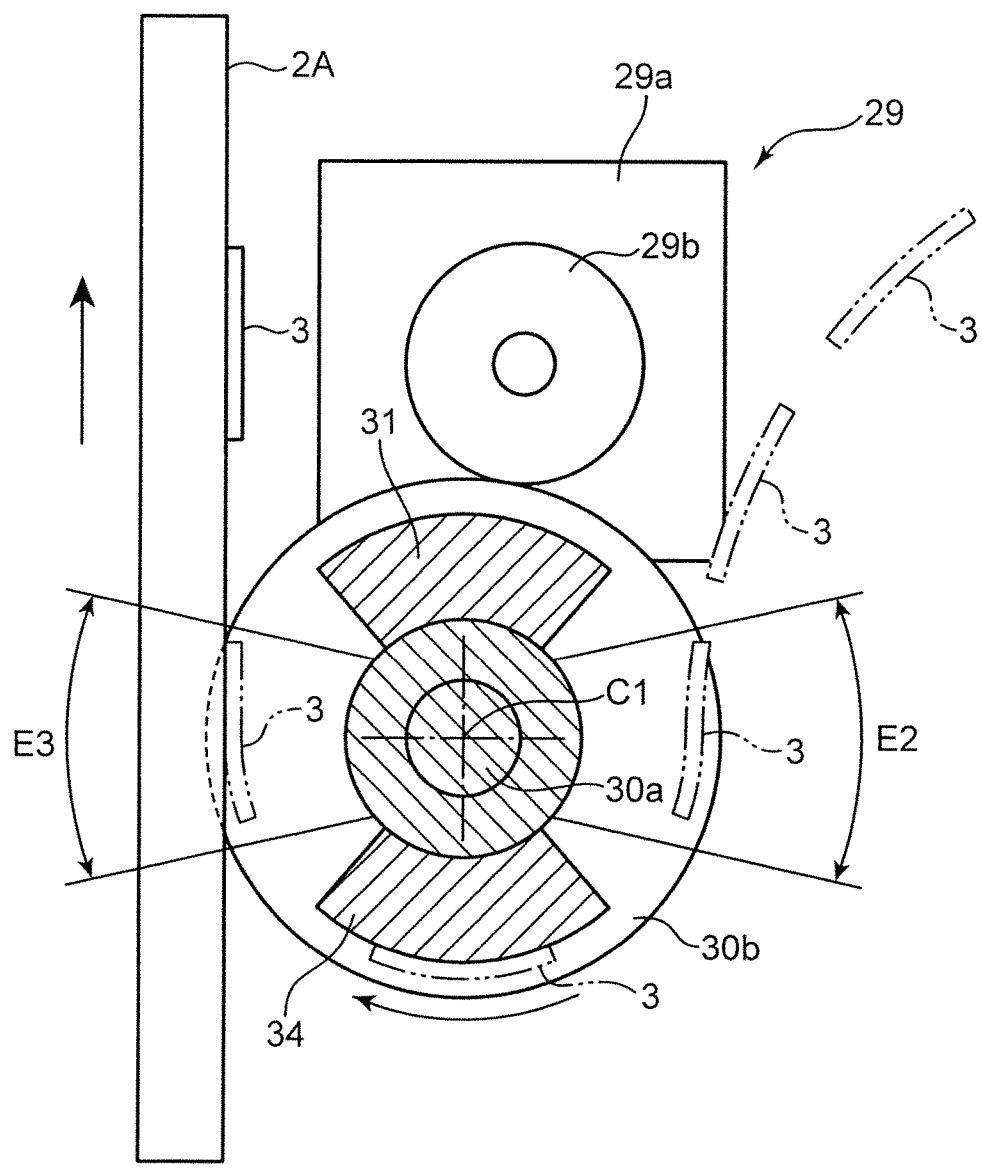
FIG. 8 is a cross section along VIII-VIII of FIG. 7.

Next, the rotation control device 12 will be described with reference to FIG. 7 to FIG. 9.

The rotation control device 12 is configured to rotate two second holding portions 31 and 34 which is configured to hold the absorbent body 3 around the rotation center axis C1, and configured to separately adjust the angular velocity of these second holding portions 31 and 34 (and their consequent cycles). More specifically, the rotation control device 12 includes a pair of driving devices 24 and 25 respectively provided with the second holding portions 31 and 34, a control unit 26 (see FIG. 9) that controls the driving operation of the driving devices 24 and 25, an input unit 27 (see FIG. 9) for inputting instructions to the control unit 26, and a rotation angle detector 28 (see FIG. 9) that is configured to detect a rotation angle of each of the second holding portions 31 and 34.

The driving device 24 includes a servo motor (holding portion drive source) 29, a drive shaft 30 configured to drive by the power of the servo motor 29, and the second holding portion 31 configured to be rotated in response to the drive of the drive shaft 30. The servo motor 29 includes a main body 29a, and a gear 29b fixed to an output shaft that rotates relative to the main body 29a. The drive shaft 30 includes a shaft body 30a supported to be rotatable around the rotation center axis C1, and a gear 30b fixed to the shaft body 30a and meshing with the gear 29b. The second holding portion 31 is secured to the shaft body 30a. Therefore, the second holding portion 31 rotates around the rotation center axis C1 by operating the servo motor 29. A negative pressure is supplied from a suction source outside of the drawing so that the second holding portion 31 is configured to hold the absorbent body 3 by suction on its outer circumferential surface.

Similarly, the driving device 25 includes a servo motor (holding portion drive source) 32, a drive shaft 33 configured to drive by the power of the servo motor 32, and the second holding portion 34 configured to be rotated in response to the drive of the drive shaft 33. The servo motor 32 includes a main body 32a, and a gear 32b fixed to an output shaft that rotates relative to the main body 32a. The drive shaft 33 includes a shaft body 33a supported to be rotatable around the rotation center axis C1, and a gear 33b fixed to the shaft body 33a and meshing with the gear 32b. The second holding portion 34 is secured to the shaft body 33a. Therefore, the second holding portion 34 rotates around the rotation center axis C1 by operating the servo motor 32. A negative pressure is supplied from a suction source outside of the drawing so that the second holding portion 34 is configured to hold the absorbent body 3 by suction on its outer circumferential surface.

Both second holding portions 31 and 34 are disposed such that their outer circumferential surfaces (suction surfaces) are located on the same columnar surface around the rotation center axis C1. The second holding portions 31 and 34 receive absorbent bodies 3 from the first holding portions 20 of the speed change device 11 at the relay position E2, as shown in FIG. 8. Here, the second holding portion 31 or 34 sucks a surface of the absorbent body 3 opposite to surface that has been held by suction on the first holding portion 20. Namely, the second holding portion 31 or 34 holds, by suction, the surface of the absorbent body 3 opposite to the surface where adhesive has been applied. While the rotation control device 12 described in this embodiment has two second holding portions 31 and 34, the rotation control device 12 may have one second holding portion, or three or more second holding portions.

Figure 15:
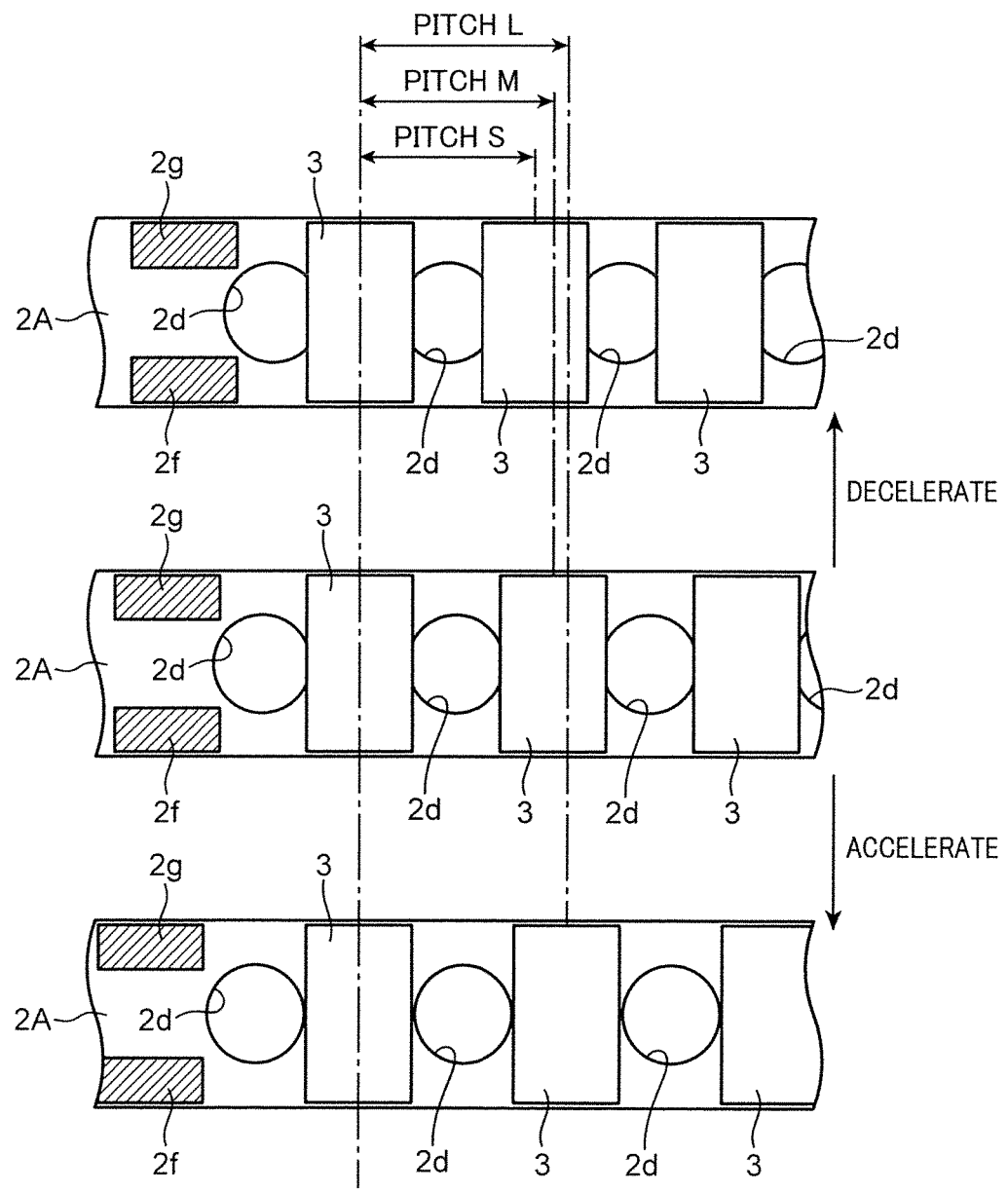
FIG. 15 is a diagram for explaining a result of speed control performed in the process steps shown in FIG. 14.

The control unit 26 controls the angular velocity of the second holding portions 31 and 34 so as to change the pitch of absorbent bodies 3 on the body web 2A for each size of the disposable diaper 1. More specifically, pitch S for size S is smaller than pitch M for size M and pitch L for size L, and pitch M is smaller than pitch L, as shown in FIG. 15. To change the pitch, it is necessary to control the angular velocity of each of the second holding portions 31 and 34 at the transfer position E3 for each size while maintaining the cycles of the second holding portions 31 and 34 arriving at the transfer position E3. More specifically, the larger size the disposable diaper 1 has, the higher angular velocity of the second holding portions 31 and 34 is needed. In the body web transport step (1), the body web 2A is transported at a speed that allows the absorbent bodies 3 to be received from the second holding portions at the transfer position E3. Namely, the transport speed of the body web 2A at the transfer position E3 is controlled in accordance with the angular velocity of the second holding portions 31 and 34 for each size.

Figure 9:
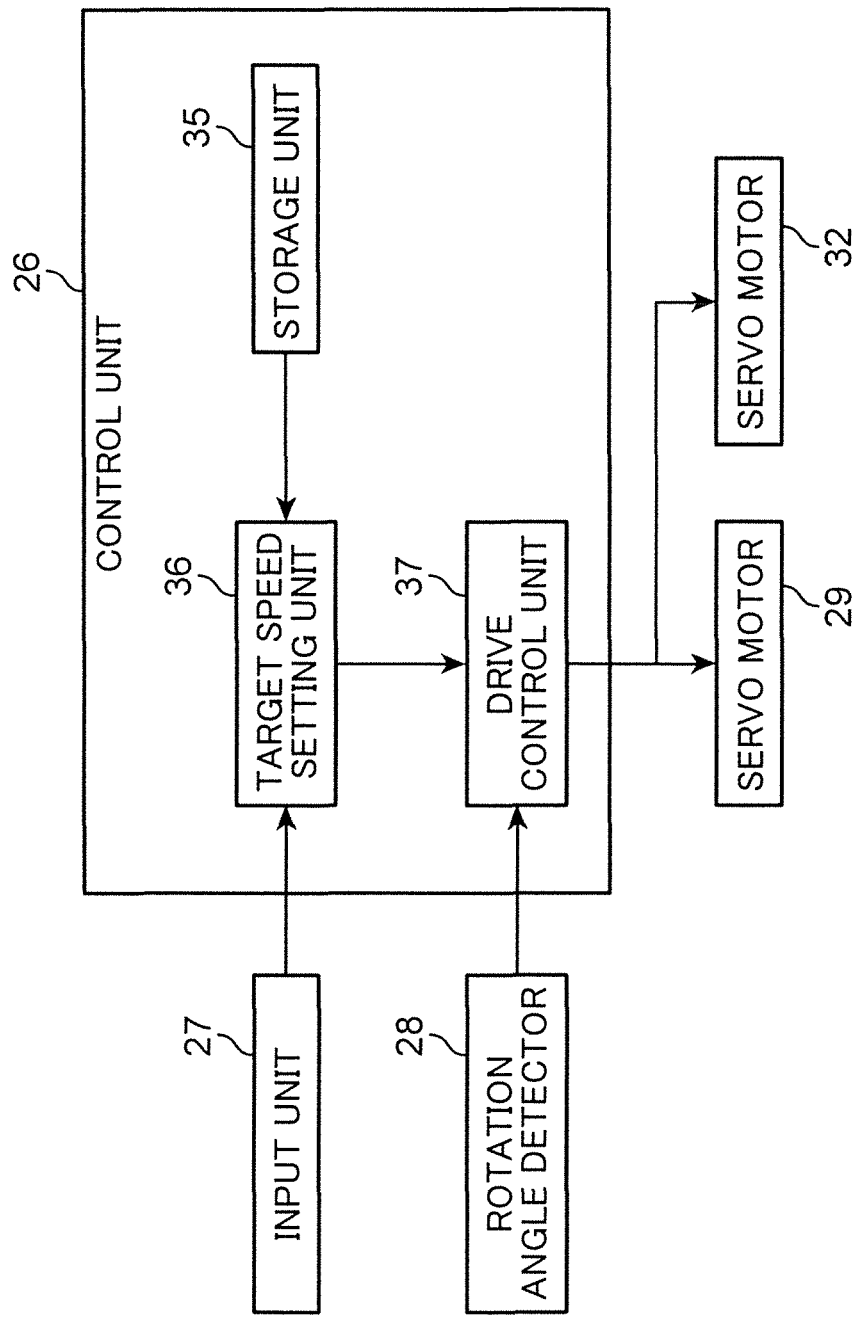
FIG. 9 is a block diagram illustrating an electrical configuration of the rotation control device shown in FIG. 4.

More specifically, the control unit 26 includes a storage unit 35 that stores information on angular velocities of the servo motors 29 and 32, a target speed setting unit 36 that sets target speeds to be achieved by the servo motors 29 and 32 based on the information stored in the storage unit 35, and a drive control unit 37 that controls the speeds of the servo motors 29 and 32 to achieve the target speeds set by the target speed setting unit 36, as shown in FIG. 9.

Figure 10:
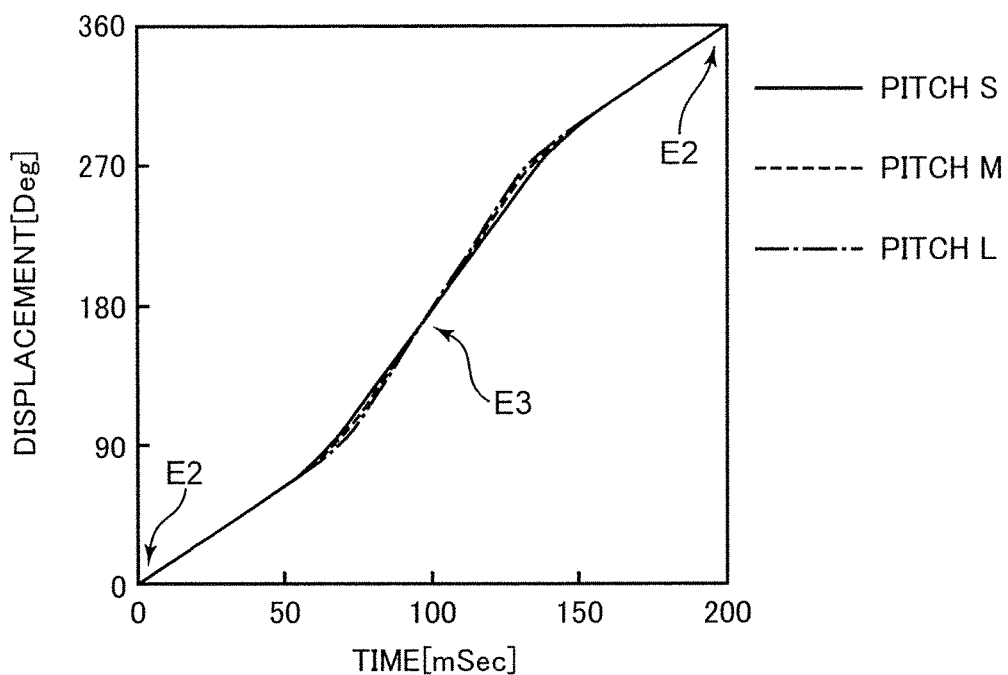
FIG. 10 is a graph showing information on amount of displacement stored in a storage unit shown in FIG. 9.
Figure 11:
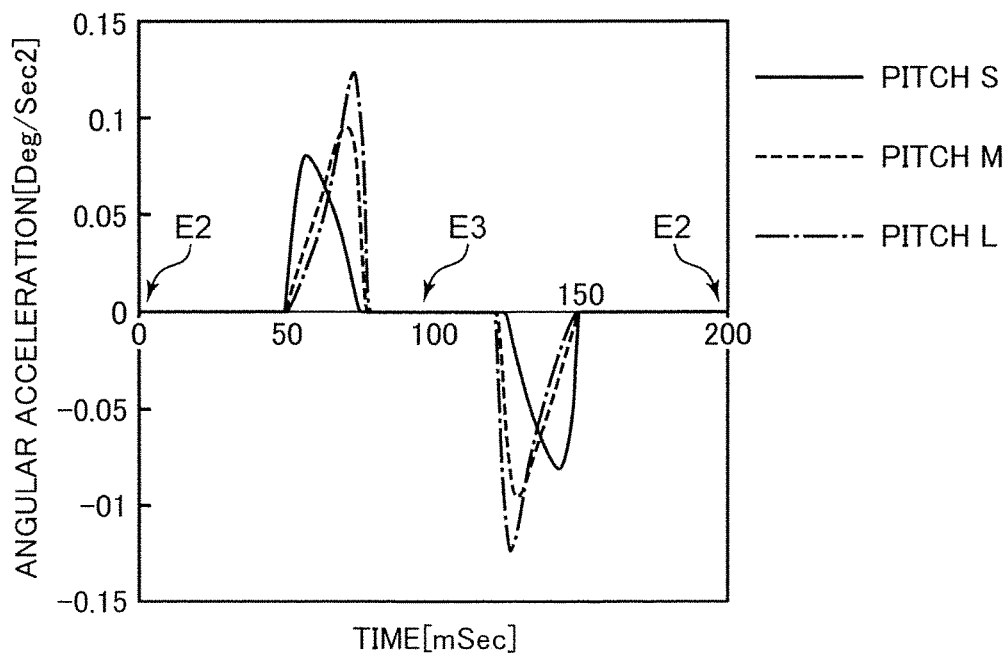
FIG. 11 is a graph showing information on angular acceleration stored in the storage unit shown in FIG. 9.
Figure 12:
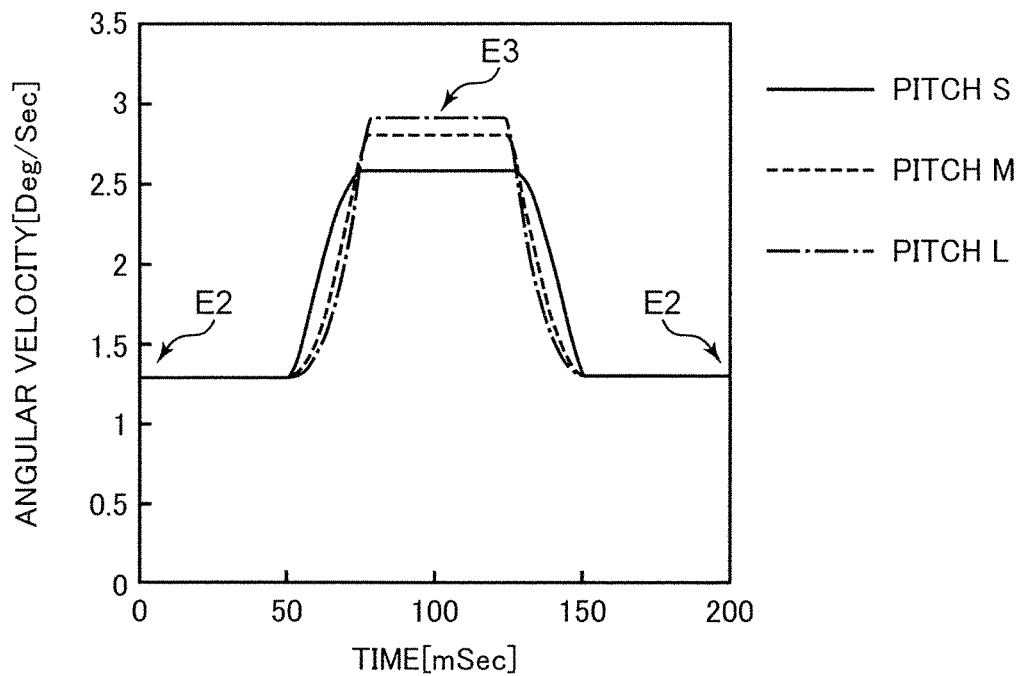
FIG. 12 is a graph showing information on angular velocity stored in the storage unit shown in FIG. 9.
Figure 13:
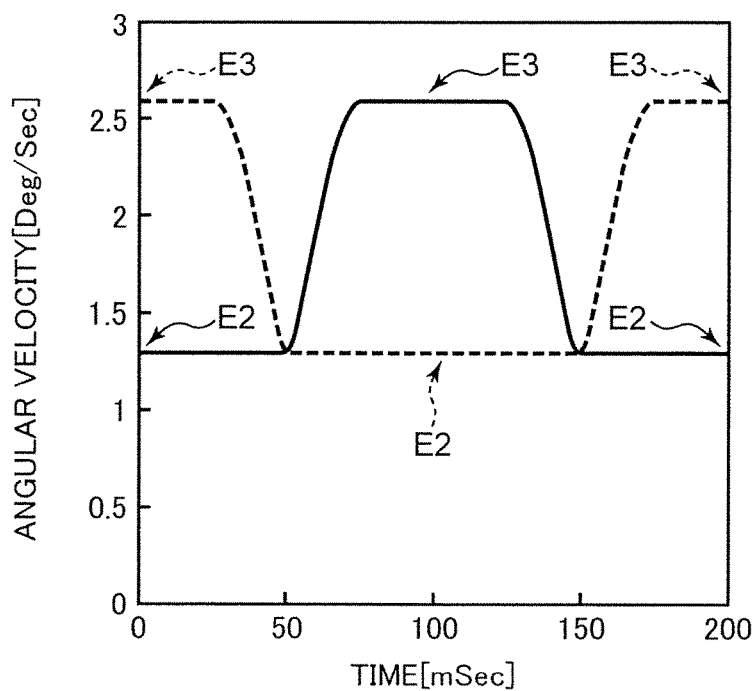

The storage unit 35 stores such information on angular velocities of servo motors 29 and 32 as shown in FIG. 10 to FIG. 13. Referring to FIG. 10 to FIG. 12, one of the second holding portions 31 and 34 arrives at the relay position E2 at around 0 ms and 200 ms, and arrives at the transfer position E3 at around 100 ms. Namely, according to the graphs in FIG. 10 to FIG. 12, the amount of displacement, angular acceleration, and angular velocity of the second holding portions 31 and 34 are each set so that the second holding portions 31 and 34 arrive at the relay position E2 and the transfer position E3 at the same cycle (cycle of 200 ms) for each pitch. In FIG. 13, the angular velocity of one of the second holding portions 31 and 34 is indicated by a solid line, and the angular velocity of the other one of the second holding portions 31 and 34 is indicated by a broken line. As is seen from FIG. 13, a phase shift of 180° is provided between the second holding portions 31 and 34. As shown in FIG. 12, the larger size the disposable diaper 1 has, the higher transfer speed of the second holding portions 31 and 34 at the transfer position E3 is set. Namely, the transfer speed is progressively higher for pitch S, pitch M, and pitch L. The receiving speed of the second holding portions 31 and 34 at the relay position E2 is set such that the second holding portion 31 and 34 can receive absorbent bodies from the first holding portions 20. More specifically, the receiving speed is set in accordance with the angular velocity of the first holding portions 20 at the relay position E2. In this embodiment, as shown in FIG. 12, the transfer speed is higher than the receiving speed for all the pitches. That is, the angular velocity of the first holding portions 20 at the relay position that is determined by the speed change mechanism of the speed change device 11 is set lower than the angular velocity corresponding to pitch S.

The target speed setting unit 36 sets a target speed based on the information stored in the storage unit 35 and read out in response to an instruction from the input unit 27. More specifically, the input unit 27 can input an instruction regarding size (instruction that specifies one of pitch S, pitch M, and pitch L). The target speed setting unit 36 reads out information corresponding to the input size from the storage unit 35 and sets a target speed based on the information. Namely, the target speed setting unit 36 changes the target speed (particularly, transfer speed) while the cycle of the second holding portions 31 and 34 is maintained (speed changing step), when an instruction regarding different sizes from the input unit 27 is input.

The drive control unit 37 controls the speed of the servo motors 29 and 32 to achieve the target speed of the second holding portions 31 and 34 (control step). More specifically, the drive control unit 37 performs feedback control on the servo motors 29 and 32 based on the rotation angles of the servo motors 29 and 32 detected by the rotation angle detector 28.

Figure 14:
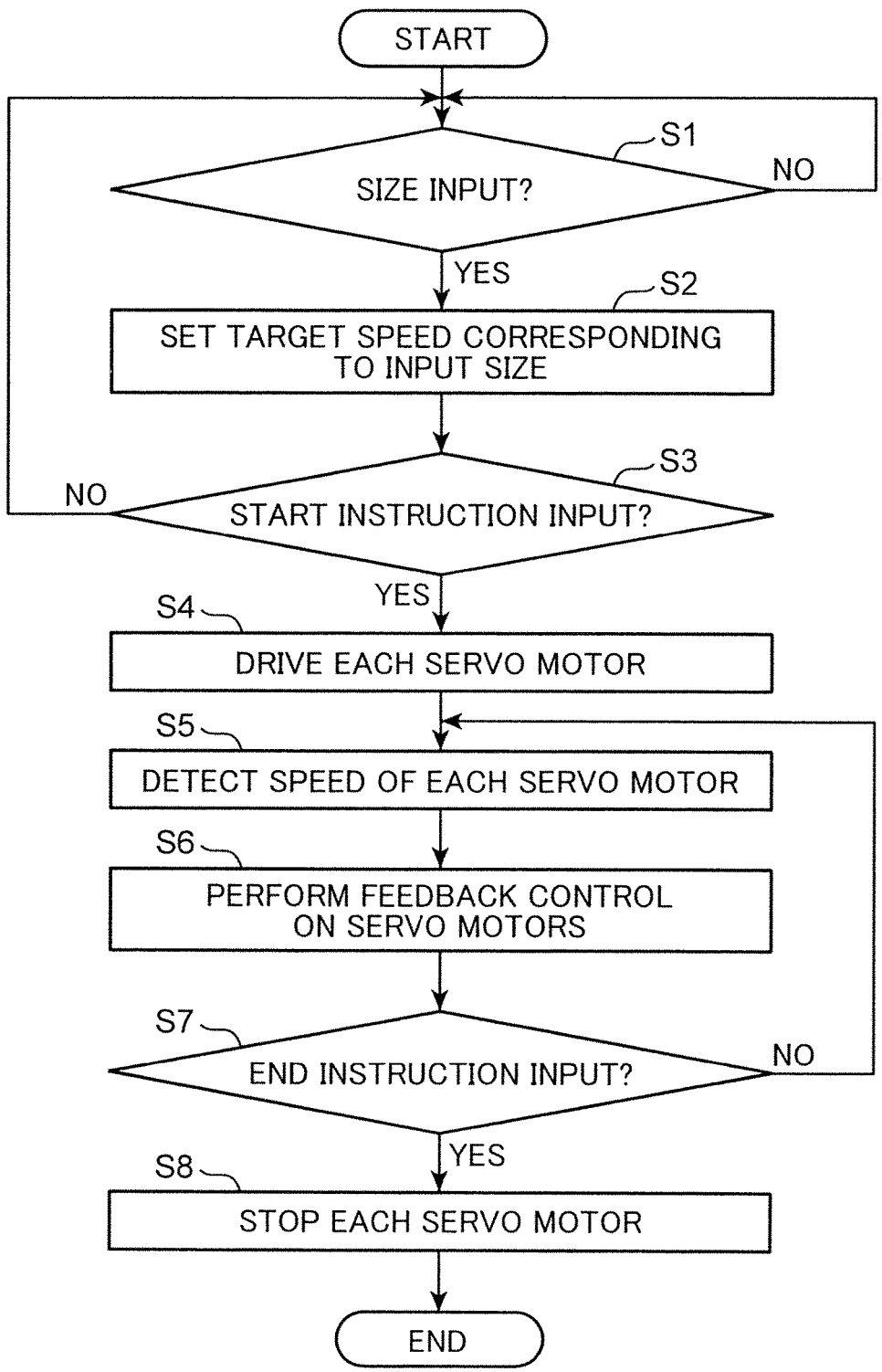
FIG. 14 is a flowchart showing process steps executed by a control unit shown in FIG. 9.

Next, the process steps performed by the control unit 26 will be described with reference to FIG. 14.

Once the process by the control unit 26 starts, an input of an instruction regarding size from the input unit 27 is waited for (step S1). When a size instruction is input (YES at step S1), a target speed corresponding to the input size is set (step S2). That is, at step S2, a value corresponding to size is extracted from information stored in the storage unit 35 such as those shown in FIG. 10 to FIG. 13 and set the target speed based on the information.

Next, it is determined whether or not a Start instruction has been input from the input unit 27 (step S3). If it is determined that the Start instruction has not been input yet (NO at step S3), step S1 is carried out repeatedly. On the other hand, if the Start instruction is input (YES at step S3), both servo motors 29 and 32 are driven (step S4).

When the servo motors 29 and 32 are driven, the speed of each servo motor 29 or 32 is detected (step S5). Feedback control of both servo motors 29 and 32 is performed based on the detected speeds (step S6).

It is then determined whether or not an End instruction has been input from the input unit 27 (step S7). If it is determined that the End instruction has not been input yet, step S5 is carried out repeatedly. On the other hand, if it is determined that the End instruction has been input, the servo motors 29 and 32 are stopped (step S8) and the process ends.

Figure 4:
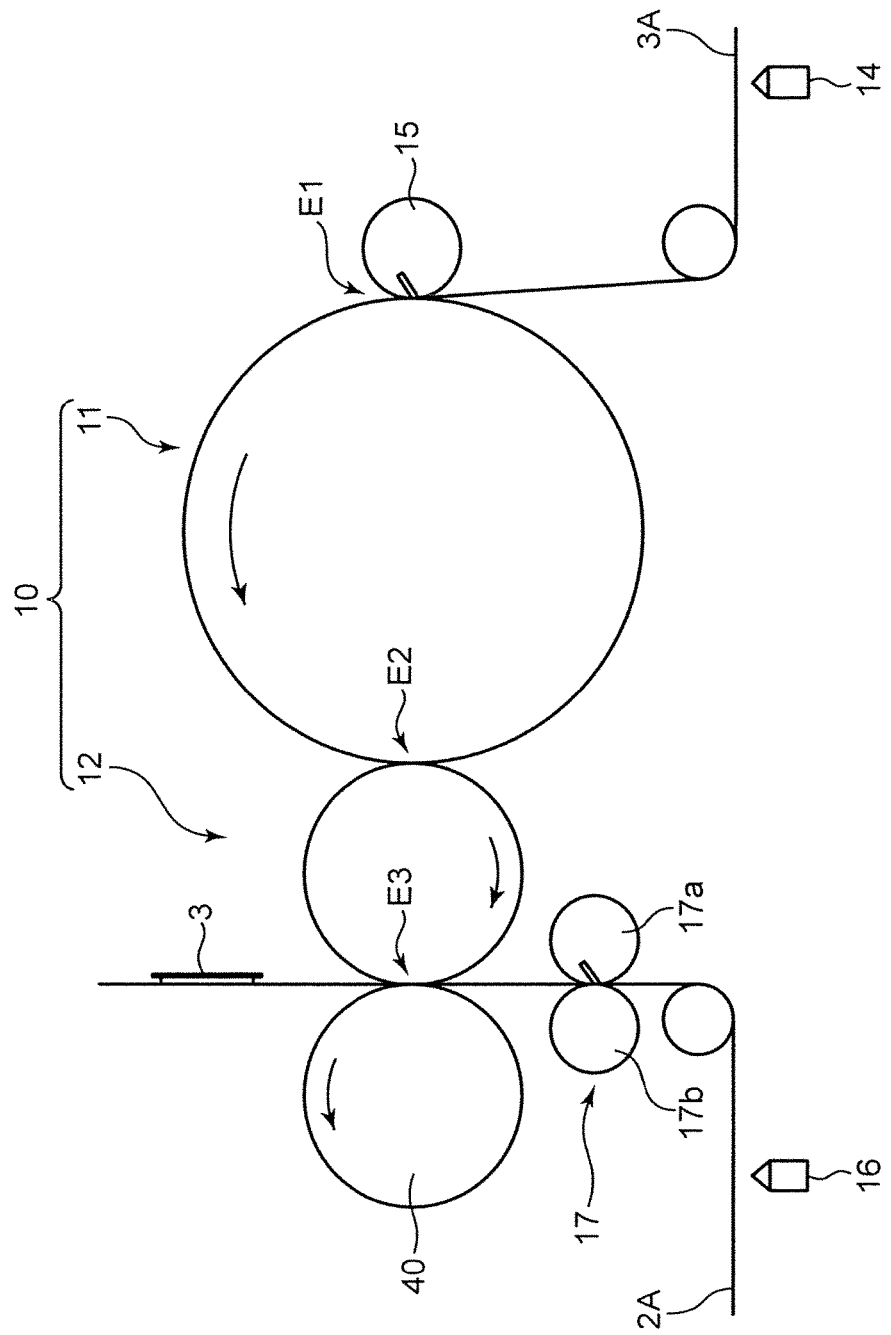
FIG. 4 is a schematic diagram illustrating part of a device used in the manufacturing method shown in FIG. 3.
Figure 5:
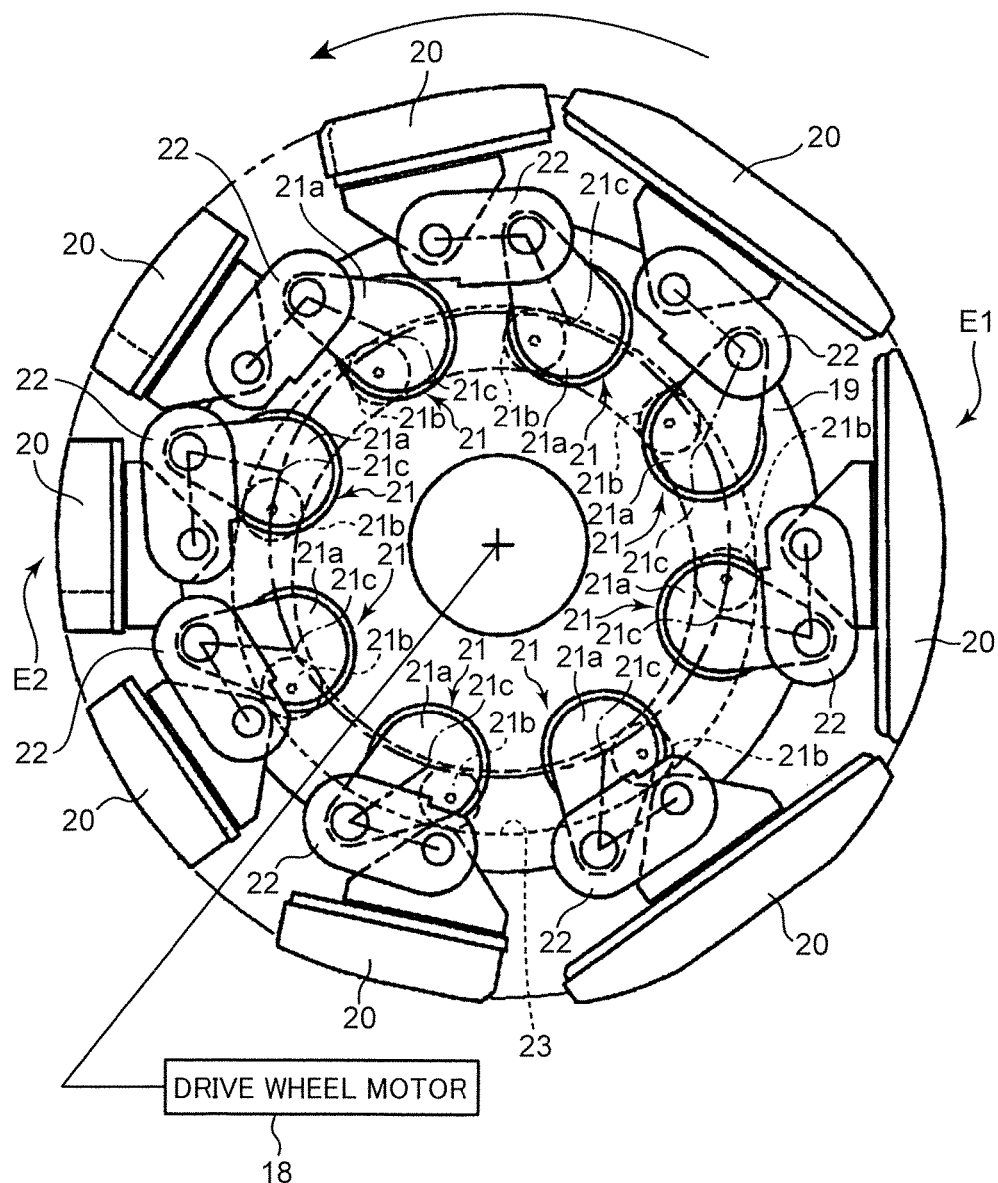
FIG. 5 is a schematic diagram illustrating a speed change device shown in FIG. 4 to a larger scale.

As described above, absorbent bodies 3 transported by the transport device 10 are joined to the body web 2A in the joining step (8) as shown in FIG. 3 and FIG. 4.

In the joining step (8), the absorbent body 3 is joined to the body web 2A in a state where the absorbent body 3 is placed between two adjacent leg holes 2d such as to cover inner side portions of these two leg holes 2d. Here, both end portions in the longitudinal direction of the absorbent body 3 are positioned on the outer sides of the leg holes 2d in the width direction of the body web 2A. More specifically, in this embodiment, the body web 2A and the absorbent body 3 are pressed against each other between a pressure roller 40 and the rotation control device 12 (second holding portions 31 and 34), as shown in FIG. 4. Thereby, the body web 2A and the absorbent body 3 are joined together by the adhesive that has been applied in the first application step (2) and the second application step (5).

In the folding step (9), the body web 2A is folded over so that the absorbent body 3 is folded in two.

In the side seal step (10), the folded layers of the body web 2A are thermally bonded together, to form the side seals 2e.

In the body cutting step (11), the body web 2A is cut to individual disposable diapers 1 such that the side seals 2e are left on the left and right of each disposable diaper 1.

As described above, according to the embodiment, the pitch between absorbent bodies 3 joined to the body web 2A can be changed, so that wearable articles (disposable diaper 1 in this embodiment) of various sizes having the diaper body 2 with different areas relative to the absorbent body 3 can be manufactured easily.

More specifically, in the embodiment, the speed of the first holding portions 20 is varied by the speed change mechanism, as well as the speed of the second holding portions 31 and 34 that receive absorbent bodies 3 from the first holding portions 20 is controlled by the rotation control device 12. Thereby, the absorbent bodies 3 can be transported to the transfer position E3 such that the speed of the absorbent bodies 3 varies between the receiving position E1 and the transfer position E3.

In the embodiment described above, moreover, the transfer speed of the second holding portions 31 and 34 can be changed, while the cycles of the second holding portions 31 and 34 are maintained. Thus, the speed of the absorbent body 3 at the relay position, which is determined by the speed change mechanism, can be changed to a different transfer speed, while the cycles of the second holding portions 31 and 34 are maintained. Therefore, according to the embodiment, absorbent bodies 3 can be transported to the transfer position at various different speeds, while the quantity of the absorbent bodies 3 to be transported per unit time is maintained.

As the absorbent bodies 3 are joined to the body web 2A at different transfer speeds while the cycles are maintained, the absorbent bodies 3 are joined to the body web 2A at different pitches.

While a disposable diaper 1 was described as one example in the above embodiment, other wearable articles (e.g., sanitary products) of various sizes having a basic part with different areas relative to one processing part can be manufactured with the use of the transport device 10 described above.

According to the embodiment described above, the body web 2A and the absorbent body 3 are joined together with the adhesive, since the adhesive is applied to both of them in the first application step (2) and the second application step (5). Note, the body web 2A and the absorbent body 3 can be joined together by applying adhesive to at least one of them.

In the embodiment described above, the adhesive is applied to areas of the body web 2A other than regions where leg holes 2d are to be formed, in the first application step (2). This prevents deterioration of cutting performance by the cutting blades of the rotary cutter 17a for forming leg holes 2d in the body web 2A, the deterioration of cutting performance may be caused by adhesive adhered on the cutting blades.

In the embodiment described above, the adhesive is applied to two web-side bonding positions corresponding to both end portions of the absorbent body 3 in the web width direction (positions corresponding to the front bonding portion 2f and the rear bonding portion 2g), and to a position between these web-side bonding positions (position corresponding to the center bonding portion 3a). Thus the adhesive is disposed in a wide area of the absorbent body 3 in the web width direction. This way, the bond strength between the absorbent body 3 and the body web 2A can be enhanced, while deterioration of cutting performance by the cutting blades of the rotary cutter 17a is prevented, as described above.

While the adhesive is applied only to the front bonding portion 2f and the rear bonding portion 2g of the body web 2A in the embodiment described above, the invention is not limited to this. For example, the adhesive may be applied to areas other than regions where leg holes 2d are to be formed, between the front bonding portion 2f and the rear bonding portion 2g of the body web 2A. In this case, the second application step (5) of applying adhesive to the absorbent body 3 can be omitted.

In the embodiment described above, while the first holding portions 20 hold by suction a portion on the adhesive-applied surface of the absorbent body 3 other than the part applied with adhesive, the second holding portions 31 and 34 hold a surface opposite to the adhesive-applied surface of the absorbent body 3 by suction. Thereby, the absorbent body 3 can be transferred from the second holding portions 31 and 34 to the body web 2A at the transfer position E3 with the adhesive oriented toward the body web 2A. Thus the absorbent body 3 can be joined to the body web 2A while avoiding contact between the adhesive applied on the absorbent body 3 and the holding portions 20, 31, and 34.

In the embodiment described above, in particular, the adhesive is disposed on a portion corresponding to the center bonding portion 3a of the absorbent body 3 in the second application step (5). Therefore, the first holding portion 20 can hold both end portions of the absorbent body 3 by suction, as shown in FIG. 6. This way, the first holding portion 20 can hold the absorbent body 3 in a more stable orientation.

In the embodiment described above, as shown in FIG. 12, the transfer speed is higher than the receiving speed for all the pitches. That is, the angular velocity of the first holding portions 20 at the relay position that is determined by the speed change mechanism of the speed change device 11 is set lower than the angular velocity corresponding to pitch S. However, the angular velocity of the first holding portions 20 at the relay position E2 of the speed change device 11 may preferably be set between an upper limit value of angular velocity to be conceived as the transfer speed (angular velocity corresponding to pitch L) and a lower limit value of angular velocity to be conceived as the transfer speed (angular velocity corresponding to pitch S). That is, it is preferable to prepare the speed change mechanism to achieve such speeds (preparation step). This way, a maximum amount of change in the transfer speed achieved by the servo motors 29 and 32 can be reduced as compared to the case in which the angular velocity of the first holding portions 20 at the relay position E2 is set to a value that falls out of the range between the upper limit value and lower limit value, as in the embodiment described above. Load on the servo motors 29 and 32 is accordingly reduced, and the time required for changing the transfer speed is shortened.

For example, if the angular velocity of the first holding portions 20 at the relay position E2 is set to a value corresponding to pitch M, then the pitch may be adjusted in the following manner. Specifically, when the absorbent bodies 3 are joined to the body web 2A at pitch M, the receiving speed and the transfer speed of the second holding portions 31 and 34 may be set equal. The second holding portions 31 and 34 is accelerated in such a manner that the transfer speed of the second holding portions 31 and 34 become higher than the transfer speed set for pitch M as shown in FIG. 15, thereby disposable diapers 1 can be manufactured at pitch L. The second holding portion 31 and 34 is decelerated in such a manner that the transfer speed of the second holding portions 31 and 34 become lower than the transfer speed set for pitch M, thereby disposable diapers 1 can be manufactured at pitch S.

Furthermore, the angular velocity of the first holding portions 20 at the relay position E2 should most preferably be set within a predetermined range containing an intermediate value between the upper limit value and lower limit value noted above. This way, the amount of change in the transfer speed achieved by the servo motors 29 and 32 when joining the absorbent bodies 3 at pitch S and when joining the absorbent bodies 3 at pitch L is made substantially the same. The maximum amount of change in the transfer speed achieved by the servo motors 29 and 32 is therefore minimized.

While the speed change device 11 described in the embodiment has eight first holding portions 20, the number of the first holding portions 20 is not limited to this. Provided that the speed is varied between the receiving position E1 and the relay position E2, there may be at least one first holding portion 20.

The specific embodiments described above generally include the invention having the following configurations.

To solve the problems mentioned above, the present invention provides a transport method of transporting a processing part from a predetermined receiving position to a predetermined transfer position, the transport method including: a speed varying step of varying speed of a first holding portion between the receiving position and a predetermined relay position by means of a speed change mechanism, by rotating, at constant speed, a drive wheel on which the first holding portion that is configured to receive the processing part at the receiving position is supported via the speed change mechanism; a control step of controlling speed of a holding portion drive source for driving rotation of a second holding portion configured to hold the processing part, such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle; and a speed changing step of changing the transfer speed while the cycle is maintained.

The present invention also provides a transport device for transporting a processing part from a predetermined receiving position to a predetermined transfer position, the transport device including: a speed change device including a first holding portion configured to receive a processing part at the receiving position, a drive wheel supporting the first holding portion, a drive source for the drive wheel for rotating the drive wheel at constant speed, and a speed change mechanism interposed between the first holding portion and the drive wheel to vary speed of the first holding portion between the receiving position and a predetermined relay position as the drive wheel rotates at constant speed; and a rotation control device including a second holding portion configured to hold the processing part, a holding portion drive source for driving rotation of the second holding portion, and a control unit that controls speed of the holding portion drive source such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle, wherein the control unit of the rotation control device is configured to change the transfer speed while maintaining the cycle.

According to the transport method and transport device of the present invention, the speed of the first holding portion is varied by the speed change mechanism, as well as the speed of the second holding portion that receives the processing part from the first holding portion is controlled. Thereby, the processing part can be transported to the transfer position such that the speed of the processing part varies between the receiving position and the transfer position.

According to the transport method and transport device, moreover, the transfer speed of the second holding portion can be changed, while the cycle of the second holding portion is maintained. Thus, the speed of the processing part at the relay position, which is determined by the speed change mechanism, can be changed to a different transfer speed, while the cycle of the second holding portion is maintained. Therefore, according to the transport method and transport device, processing parts can be transported to a transfer position at various different speeds while the quantity of the processing parts to be transported per unit time is maintained.

Note, the term "predetermined cycle" in the present invention corresponds to a time interval between successive arrivals of a plurality of first holding portions at the relay position. More specifically, the "predetermined cycle" is determined by the speed change mechanism in the speed change device and the rotational speed of the drive source for the drive wheel.

Preferably, the transport method may further include a preparation step of preparing the speed change mechanism such that the speed of the first holding portion at the relay position is set between a predetermined upper limit value and a predetermined lower limit value of the transfer speed.

In the transport device, preferably, the speed change mechanism of the speed change device may vary the speed of the first holding portion such that the speed of the first holding portion at the relay position is between a predetermined upper limit value and a predetermined lower limit value of the transfer speed.

According to the transport method and transport device, the speed of the first holding portion at the relay position is set between an upper limit value and a lower limit value expected as the transfer speed. This way, a maximum amount of change in the transfer speed achieved by the holding portion drive source can be reduced as compared to the case in which the speed of the first holding portion at the relay position is set to a value that falls out of the range between the upper limit value and the lower limit value. Load on the holding portion drive source is accordingly reduced, and the time required for changing the transfer speed is shortened.

Furthermore, the present invention provides a method of manufacturing a disposable wearable article having a basic part and a processing part joined on the basic part, the method including: a web transport step of transporting a basic part web for forming the basic part; a processing part transport step of transporting the processing part from a predetermined receiving position to a predetermined transfer position, such that the processing part is received at the receiving position and transferred, at the transfer portion, onto the basic part web that is being transported in the web transport step; a joining step of joining the processing part to the basic part web; and a cutting step of cutting the basic part web to the basic part, wherein the processing part transport step includes: a speed varying step of varying speed of a first holding portion between the receiving position and a predetermined relay position by means of a speed change mechanism, by rotating, at constant speed, a drive wheel on which the first holding portion that is configured to receive the processing part at the receiving position is supported via the speed change mechanism; a control step of controlling speed of a holding portion drive source for driving rotation of a second holding portion configured to hold the processing part, such that speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle; and a speed changing step of changing the transfer speed while the cycle is maintained, and wherein, in the web transport step, the basic part web is transported at a speed that allows the processing part to be received at the transfer position.

According to the method of manufacturing a disposable wearable article of the present invention, the pitch between processing parts joined on the basic part web can be changed, so that wearable articles (e.g., disposable diaper or sanitary product) of various sizes having a basic part with different areas relative to the processing part can be manufactured easily.

More specifically, in the manufacturing method, the speed of the first holding portion is varied by the speed change mechanism in the speed varying step, as well as the speed of the second holding portion that receives the processing part from the first holding portion is controlled in the control step. Thereby, the processing part can be transported to the transfer position such that the speed of the processing part varies between the receiving position and the transfer position.

In the manufacturing method, moreover, the transfer speed of the second holding portion can be changed while the cycle of the second holding portion is maintained, in the speed changing step. Thus, the speed of the processing part at the relay position, which is determined by the speed change mechanism, can be changed to a different transfer speed, while the cycle of the second holding portion is maintained. Therefore, according to the present invention, processing parts can be transported to a transfer position at various different speeds while the quantity of the processing parts to be transported per unit time is maintained.

As the processing parts are joined to the basic part web at the same cycle but at different transfer speeds, the processing parts can be joined to the basic part web at different pitches.

Preferably, the method of manufacturing a wearable article may further include an application step of applying an adhesive to at least one of the basic part web and the processing part, so that the basic part web and the processing part are joined together with the adhesive in the joining step.

According to this manufacturing method, the basic part web and the processing part can be joined together with the adhesive, as the adhesive is applied to at least one of the basic part web and the processing part.

Preferably, the method of manufacturing a disposable wearable article may further include a through hole forming step of forming a plurality of through holes in the basic part web at a distance in a transport direction of the basic part web, and the processing part and the basic part web may be joined together in the joining step in a state where the processing part is placed between two adjacent through holes such as to cover inner side portions of the two through holes, and in the application step, the adhesive may be applied before the through hole forming step in areas other than regions where the through holes are to be formed in the basic part web.

In this manufacturing method, the adhesive is applied in the application step to areas of the basic part web other than regions where through holes are to be formed. This prevents deterioration of cutting performance by the cutting blades for forming through holes in the basic part web, the deterioration of cutting performance may be caused by adhesive adhered on the cutting blades.

In the method of manufacturing a disposable wearable article, preferably, the processing part may be bonded to the basic part web in the joining step such that both ends of the processing part are placed on outer sides of the through holes in a web width direction orthogonal to the transport direction of the basic part web, and in the application step, the adhesive may be applied before the through hole forming step to two web-side bonding positions on the basic part web where both ends of the processing part in the web width direction are placed, and the adhesive is applied before the joining step to a portion of the processing part, which is a portion other than a portion that covers the through holes and is placed between the web-side bonding positions.

In this manufacturing method, the adhesive is applied to two web-side bonding positions corresponding to both ends of the processing part in the web width direction, and to a position between these web-side bonding positions. Thereby, the adhesive is deposited in a wide area of the processing part in the web width direction. This way, the bond strength between the processing part and the basic part web can be enhanced, while deterioration of cutting performance by the cutting blades is prevented, as described above.

In the method of manufacturing a disposable wearable article, preferably, in the speed varying step, both ends of the processing part in the web width direction on a surface applied with the adhesive may be held by suction by the first holding portion, and in the control step, a surface opposite to the surface applied with the adhesive of the processing part may be held by suction by the second holding portion.

In the method of manufacturing a disposable wearable article, preferably, in the application step, the adhesive may be applied at least to the processing part among the basic part web and the processing part, and in the speed varying step, a portion of the processing part on a surface applied with the adhesive other than an adhesive-applied portion may be held by suction by the first holding portion, and in the control step, a surface opposite to the surface applied with the adhesive of the processing part may be held by suction by the second holding portion.

In the manufacturing method, while the first holding portion holds by suction a portion on a surface applied with adhesive of the processing part other than the part applied with adhesive, the second holding portion holds the surface opposite to the surface applied with adhesive of the processing part by suction. Thereby, the processing part can be transferred from the second holding portion to the basic part web at the transfer position with the adhesive oriented toward the basic part web. Thus the processing part can be joined to the basic part web while contact between the adhesive applied on the processing part and each of the holding portions is avoided.

In particular, when adhesive has been deposited in the application step on a portion of the processing part that is placed between the web-side bonding positions, both ends of the processing part can be held by suction by the first holding portion. In this case, therefore, the first holding portion can hold the processing part in a more stable orientation.

The present invention also provides a wearable article manufactured by the manufacturing method described above.

INDUSTRIAL APPLICABILITY

According to the present invention, processing parts can be transported to a transfer position at various different speeds while the quantity of the processing parts to be transported per unit time is maintained.

E1: Receiving position
E2: Relay position
E3: Transfer position
1: Disposable diaper (wearable article)
2: Leg hole (through hole)
2: Diaper body (basic part)
2A: Body web (basic part web)
2d: Leg hole (through hole)
2f: Front bonding portion (corresponding to a web-side bonding position)
2g: Rear bonding portion (corresponding to a web-side bonding position)
3: Absorbent body (processed part)
3a: Center bonding portion (corresponding to a portion of the processed part placed between web-side bonding positions)
10: Transport device
11: Speed change device 12: Rotation control device
18: Drive wheel motor (drive source for the drive wheel)
19: Drive wheel
20: First holding portion
21: Crank arm (speed change mechanism)
22: Link (speed change mechanism)
23: Speed-changing cam groove (speed change mechanism)
26: Control unit
29, 32: Servo motor (holding portion drive source)
31, 34: Second holding portion

The invention claimed is:

1. A method of manufacturing a disposable wearable article having a basic part and a processing part joined on the basic part, the method comprising:
   a web transport step of transporting a basic part web for forming the basic part;
   a processing part transport step of transporting the processing part from a predetermined receiving position to a predetermined transfer position, such that the processing part is received at the receiving position and transferred, at the transfer portion, onto the basic part web that is being transported in the web transport step;
   a joining step of joining the processing part to the basic part web; and
   a cutting step of cutting the basic part web to the basic part, wherein
   the processing part transport step includes:
   a speed varying step of varying a speed of a first holding portion between the receiving position and a predetermined relay position by means of a speed change mechanism, the first holding portion being configured to receive the processing part at the receiving position, the speed varying step being carried out by rotating, at constant speed, a drive wheel on which the first holding portion is supported via the speed change mechanism, the speed changing mechanism including a crank arm rotatably attached to the drive wheel, a link rotatably attached to the crank arm and the first holding portion, and a fixed member formed with a speed-changing cam groove for swinging the crank arm;
   a control step of controlling a speed of a servo motor for driving rotation of a second holding portion that is configured to hold the processing part, such that a speed of the second holding portion becomes a receiving speed at which the second holding portion is able to receive the processing part from the first holding portion at the relay position and becomes a predetermined transfer speed at the transfer position, and such that the second holding portion arrives at the relay position and at the transfer position at a predetermined cycle; and
   a speed changing step of changing the transfer speed while the cycle and the receiving speed are maintained, and wherein,
   in the web transport step, a transport speed of the basic part web is changed in accordance with the changed transfer speed after changing the transfer speed while the cycle and the receiving speed are maintained in the speed changing step.

2. The method of manufacturing a disposable wearable article according to claim 1, further comprising an application step of applying an adhesive to at least one of the basic part web and the processing part, wherein
   the basic part web and the processing part are joined together by the adhesive in the joining step.

3. The method of manufacturing a disposable wearable article according to claim 2, further comprising a through hole forming step of forming a plurality of through holes in the basic part web at a distance in a transport direction of the basic part web, wherein
   the processing part and the basic part web are joined together in the joining step in a state where the processing part is placed between two adjacent through holes such as to cover inner side portions of the two through holes, and
   in the application step, the adhesive is applied before the through hole forming step in areas other than regions where the through holes are to be formed in the basic part web.

4. The method of manufacturing a disposable wearable article according to claim 3, wherein the processing part is bonded to the basic part web in the joining step such that both ends of the processing part are placed on outer sides of the through holes in a web width direction orthogonal to the transport direction of the basic part web, and
   in the application step, the adhesive is applied before the through hole forming step to two web-side bonding positions on the basic part web where both ends of the processing part in the web width direction are placed, and the adhesive is applied before the joining step to a portion of the processing part, which is a portion other than a portion that covers the through holes and is placed between the web-side bonding positions.

5. The method of manufacturing a disposable wearable article according to claim 4, wherein, in the speed varying step, both ends of the processing part in the web width direction on a surface applied with the adhesive are held by suction by the first holding portion, and
   in the control step, a surface opposite to the surface applied with the adhesive of the processing part is held by suction by the second holding portion.

6. The method of manufacturing a disposable wearable article according to claim 2, wherein, in the application step, the adhesive is applied at least to the processing part among the basic part web and the processing part, and
   in the speed varying step, a portion of the processing part on a surface applied with the adhesive other than an adhesive-applied portion is held by suction by the first holding portion, and
   in the control step, a surface opposite to the surface applied with the adhesive of the processing part is held by suction by the second holding portion.

* * * * *